(12) United States Patent
Hoerner (10) Patent No.: US 7,955,397 B2
(45) Date of Patent: Jun. 7, 2011

(54) SOCKET AND SLEEVE FOR ATTACHMENT TO A RESIDUAL LIMB

(75) Inventor: Jeff Hoerner, Manchester, NH (US)

(73) Assignee: BioMotions, LLC, Manchester, NH (US)

( * ) Notice: Subject to any disclaimer, the term of this patent is extended or adjusted under 35 U.S.C. 154(b) by 929 days.

(21) Appl. No.: 11/428,463

(22) Filed: Jul. 3, 2006

(65) Prior Publication Data

US 2008/0004716 A1    Jan. 3, 2008

(51) Int. Cl.
*A61F 2/80* (2006.01)
(52) U.S. Cl. .......................................................... 623/36
(58) Field of Classification Search ................ 623/32, 623/34, 37, 36
See application file for complete search history.

(56) References Cited

U.S. PATENT DOCUMENTS

| | | | |
|---|---|---|---|
| 4,923,474 A | 5/1990 | Klasson et al. | |
| 5,139,523 A | 8/1992 | Paton et al. | |
| 5,549,709 A | 8/1996 | Caspers | |
| 5,728,168 A | 3/1998 | Laghi et al. | |
| 5,888,234 A * | 3/1999 | Littig ............................ | 623/38 |
| 5,904,722 A | 5/1999 | Caspers | |
| 6,136,039 A | 10/2000 | Kristinsson et al. | |
| 6,287,345 B1 | 9/2001 | Slemker et al. | |
| 6,626,952 B2 | 9/2003 | Janusson et al. | |
| 6,645,253 B2 | 11/2003 | Caspers | |
| 6,726,726 B2 | 4/2004 | Caspers | |
| 6,761,742 B2 | 7/2004 | Caspers | |
| 6,979,355 B1 | 12/2005 | Slemker | |
| 2001/0001837 A1* | 5/2001 | Capper et al. .................. | 623/34 |
| 2004/0137178 A1 | 7/2004 | Janusson et al. | |
| 2004/0260403 A1* | 12/2004 | Patterson et al. ............. | 623/34 |
| 2005/0216095 A1 | 9/2005 | Egilsson | |

FOREIGN PATENT DOCUMENTS

| | | |
|---|---|---|
| DE | 20 60 239 | 6/1972 |
| DE | 25 40 138 A1 | 3/1977 |

OTHER PUBLICATIONS

Board, W.J. et al., "A Comparison of Trans-Tibial Amputee Suction and Vacuum Socket Conditions", *Prosthet Orthot Int*, vol. 25, pp. 202-209, 2001.
Daly, C.H. et al.,"The Effect of Pressure Loading on the Blood Flow Rate in Human Skin", *Bedsore Biomechanics*, London, MacMillan, pp. 69-77, 1976. Legro, M.W. et al., "Issues of Importance Reported by Persons with Lower Limb Amputations and Prostheses", *J Rehabil Res Dev*, vol. 36 (3), pp. 155-163, Jul. 1999.
http://www.ossur.com/template110.asp??pageid-1136, "Iceross® Seal-In Liners", printed Jun. 28, 2006.
Partial International Search Report and Invitation to Pay Additional Fees for International Application No. PCT/US2007/015049 mailed Jul. 12, 2007.
International Search Report and Written Opinion of the International Searching Authority for International Application No. PCT/US2007/015049 mailed Apr. 25, 2008.

* cited by examiner

*Primary Examiner* — Bruce E Snow
*Assistant Examiner* — Melissa Hoban
(74) *Attorney, Agent, or Firm* — Finnegan, Henderson, Farabow, Garrett & Dunner, LLP (57) ABSTRACT

A socket assembly for a prosthetic limb is provided. The socket assembly includes an elongated upper circumferential section having an open upper end and a distal end, the distal end having a distal diameter. The assembly further includes an intermediate section extending outwardly from the upper section to a maximum diameter that is larger than the distal diameter of the first upper section, the intermediate section tapering inwardly from its maximum diameter to a lower rim region. A distal section extends from the lower rim region to a base of the socket, and a one-way valve is in fluid communication with an interior of the socket assembly. A flexible diaphragm is configured to engage walls of the intermediate section.

39 Claims, 5 Drawing Sheets

SOCKET AND SLEEVE FOR ATTACHMENT TO A RESIDUAL LIMB

FIELD OF THE INVENTION

The present disclosure pertains to prostheses, and particularly to systems and methods for attaching prosthetic limbs to the body.

BACKGROUND OF THE INVENTION

Prosthetic limbs are used by thousands of patients who have had a portion of a limb amputated due to disease or injury. Generally, the prosthetic limb includes a socket and a weight-bearing portion. The patient inserts part of their remaining limb, the residual limb, into the socket to secure the prosthetic limb to the body.

The socket is generally sized to form a tight fit around the surface of the residual limb, with the goal of providing secure contact with the entire residual limb surface. By maintaining contact with as large a surface area as possible, the patient's weight is distributed over a larger surface area within the socket. This helps to ensure that the prosthetic limb maintains a secure attachment to the residual limb, allowing efficient transfer of intended movement of the residuum to the device (prosthesis).

Most patients experience some changes in the volume of the residual limb throughout the day. These changes may be caused by a variety of factors including, for example, perspiration, temperature changes, or physiologic changes due to medical problems or medications. Regardless of the cause, limb volume changes may cause the socket to fit improperly, making the prosthetic uncomfortable or causing the device to loosen or fall off. Therefore, management of limb and socket volumes is important for maintaining an appropriate fit.

One method for securing a prosthetic to a residual limb is disclosed in U.S. Pat. No. 6,726,726, which issued to Caspers on Apr. 27, 2004 (hereinafter the '726 patent). The method of the '726 patent includes creating a vacuum within the socket using a pump attached to the prosthetic limb. Although this method may provide suitable attachment of a prosthetic, it has several drawbacks. For example, to create the vacuum, the method of the '726 patent requires a mechanical pump to be attached to the prosthetic. The pump adds considerable weight to the prosthetic, making it unwieldy and/or uncomfortable for some patients. In addition, suitable pumps may be very expensive.

It is accordingly an object of the present invention to provide improved prosthetics that can produce a negative pressure within the device socket without the use of an active pump.

SUMMARY OF THE INVENTION

A socket assembly for a prosthetic limb is provided. The socket assembly includes an elongated upper circumferential section having an open upper end and a distal end, the distal end having a distal diameter. The assembly further includes an intermediate section extending outwardly from the upper section to a maximum diameter that is larger than the distal diameter of the first upper section, the intermediate section tapering inwardly from its maximum diameter to a lower rim region. A distal section extends from the lower rim region to a base of the socket, and a one-way valve is in fluid communication with an interior of the socket assembly. A flexible diaphragm is configured to engage walls of the intermediate section.

Another aspect of the present invention provides a sleeve for a residual limb. The sleeve comprises an upper tubular flexible section configured to be placed over a residual limb and a distal diaphragm securely connected to the upper flexible section and having a concave upper surface and a convex lower surface.

Another aspect of the present invention includes a method of producing a prosthetic limb socket. The method comprises producing a mold representing a residual limb and attaching a second material having a convex lower surface to the mold. The method further includes attaching a third material having a maximum diameter that is less than that of the second material and producing a socket wall conforming to the shape of the mold, including the attached second and third materials.

Another aspect of the present invention includes a method of producing a prosthetic limb socket. The method comprises applying a sleeve assembly to a residual limb, wherein the sleeve assembly includes an upper tubular flexible section configured to be placed over a residual limb and a distal diaphragm securely connected to the upper flexible section and having a concave upper surface and a convex lower surface. The method further includes producing a mold representing the residual limb and sleeve assembly, and producing a socket wall conforming to the shape of the mold.

Additional objects and advantages of the invention will be set forth in part in the description which follows, and in part will be obvious from the description or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one embodiment of the invention and together with the description, serve to explain the principles of the invention.

DESCRIPTION OF THE EMBODIMENTS

Reference will now be made in detail to the present embodiments of the invention, examples of which are illustrated in the accompanying drawings. Wherever possible, the same reference numbers will be used throughout the drawings to refer to the same or like parts.

Figure 1:
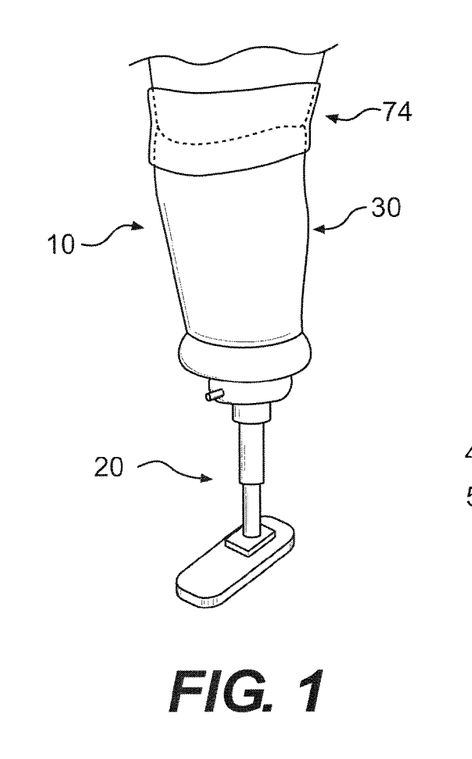
FIG. 1 illustrates a prosthetic limb, according to an exemplary embodiment of the present invention.

FIG. 1 illustrates a prosthetic limb 10, according to an exemplary embodiment. Limb 10 includes a weight-bearing portion 20 that extends from a socket 30. Socket 30 may be configured to receive a residual limb of a patient. Further, as described below, socket 30 may be designed such that a negative air-pressure is produced within socket 30 when worn by a patient.

Socket 30 may be produced from a variety of suitable synthetic materials that are fluid tight, including a number of different plastics and or resins. A prosthetic manufacture may fabricate the socket based on patient-specific anatomy and volume using techniques that employ total contact fitting protocols of the residuum. An interface sleeve/liner, between the residuum and the socket may be used. Such sleeves/liners can include fabric, foams, gel materials or combinations thereof to provide additional cushioning to the residuum.

Figure 2:
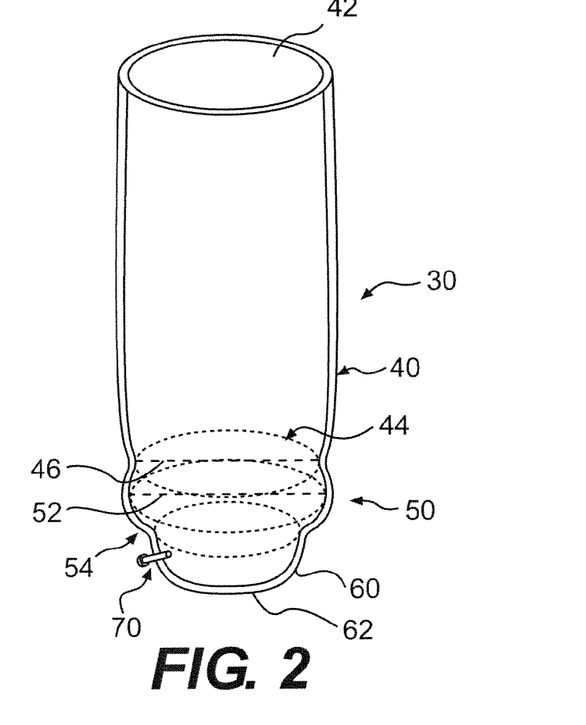
FIG. 2 illustrates a partial cut-away view of a socket assembly of the prosthetic limb of FIG. 1.

FIG. 2 illustrates a partial cut-away view of socket 30 of the prosthetic limb 10 of FIG. 1. As shown, socket 30 includes an elongated upper circumferential section 40 that is configured to receive a patient's residual limb. Upper section 40 may include an open upper end 42. As described below, in some cases it may be desirable for a patient to wear a sleeve made of fabric or another soft/pliable material over the portion of the residual limb that is inserted within upper section 40 of socket 30.

Socket 30 also includes an intermediate section 50 and a distal section 60. As shown, upper section 40 tapers inward to conform to the shape of a residual limb. Upper section 40 ends in a circumferential section 44 having a distal diameter 46. Intermediate section 50 may extend outward to form a bulged cavity having a maximum outer diameter 52 that is larger than distal diameter 44. Further, intermediate section 50 may taper inward more distally to form a lower rim region 54.

Distal section 60 may extend from lower rim 54 to a base 62 of socket 30, and may include a one-way valve 70 in fluid communication with the interior of distal section 60. As embodied herein and shown in FIG. 2, valve 70 may only allow air to flow from inside of socket 30 to outside of socket 30. Alternatively, valve 70 may include a release mechanism to allow air to flow into socket 30. The release mechanism may be used to allow air to flow into socket 30 when a patient wants to remove a residual limb from socket 30.

Figure 3A:
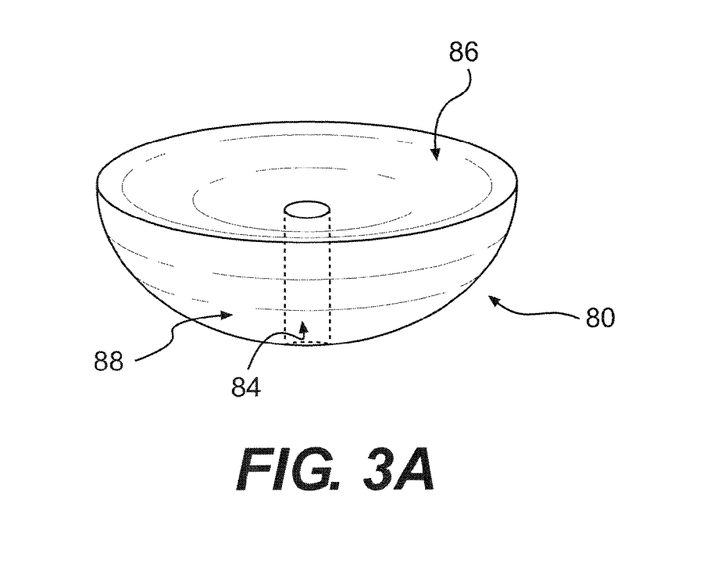
FIG. 3A illustrates a sealing diaphragm to be used with the socket of FIG. 2.
Figure 3B:
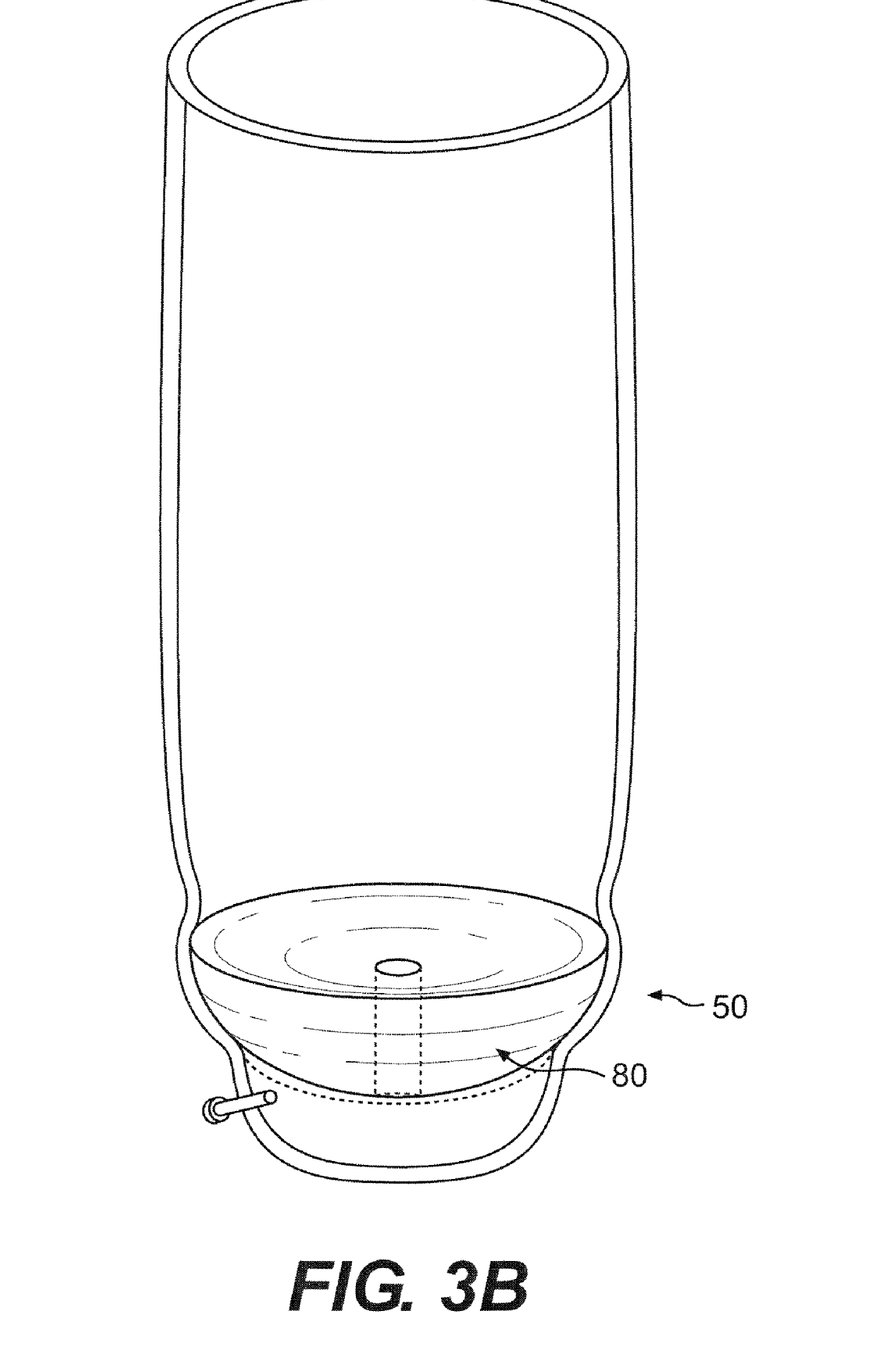
FIG. 3B illustrates the sealing diaphragm of FIG. 3A positioned within the socket of FIG. 2.

Prosthetic 10 may further include a sealing diaphragm 80, which may be configured to fit within intermediate section of socket 30. FIG. 3A illustrates an embodiment of sealing diaphragm 80 to be used with the socket of FIG. 2. The lower rim region 54 and/or lateral walls of intermediate section 50 may be shaped to conform to the diaphragm 80 so that diaphragm 80 may be positioned within intermediate section 50, as shown in FIG. 3B. Diaphragm 80 may form a tight contact with rim region 54 and/or the lateral walls of intermediate section 50. When diaphragm 80 is seated in intermediate section 50 and pressure is exerted downward on diaphragm 80, diaphragm 80 may flex downward into distal section 60. This downward pressure forces air out of valve 70, thereby producing a negative air pressure within socket 30, as the diaphragm rebounds. The negative air pressure facilitates secure attachment of socket 30 to a residual limb. The negative pressure helps to maximize contact between a limb surface or sleeve and the wall of socket 30. This will further reduce maximum contact pressure on the limb, while ensuring a continued snug fit even with limb volume changes.

It should be noted that, as shown, valve 70 is located within a lateral wall of distal section 60, but in other embodiments, valve 70 may be located within a lateral wall of intermediate section 50 or upper section 40, as long as valve 70 is in fluid communication with an interior of socket 30 where the patient's residual limb resides. In this way, a negative air pressure will still be formed as diaphragm 80 flexes downward, thereby decreasing the overall volume within socket 30, and rebounds, to expand the overall volume of socket 30.

In some embodiments, diaphragm 80 may include at least one opening 84 that will provide fluid communication through diaphragm 80. This opening will allow the negative pressure created within socket 30 to be transmitted around the limb located within socket 30. As shown, opening 84 includes one cylindrical opening, but multiple openings having any suitable shape may be selected.

The diaphragm 80 may be constructed from any material having sufficient flexibility and elasticity to allow a small degree of deflection and rebound into and out of distal section 60 during routine movements or application of weight by a patient. Suitable materials may include, for example, various polymeric materials such as silicone. For example, suitable silicone materials may include platinum-cured silicones such as Dragon Skin silicone available from Smooth-On, Inc. Further, additional materials can include various thermoplastic elastomers (e.g. Santoprene), which is available from Advanced Elastomer Systems), urethanes, ethylene vinyl acetate polymers, natural rubber, and synthetic rubber. In addition, the diaphragm can be fabricated reinforced with a internal or external matrix of plastic, composite, spring metal or fiber to control flexibility and elasticity. The diaphragm can be pre-made in various sizes to accommodate patient-specific distal residuum anatomy, or custom made from a measured, digital, or hand formed model of a residuum.

In other embodiments, diaphragm 80 may further include matrix materials to control its mechanical properties. For example, various plastic, metallic, fiber, and/or composite materials may be embedded within or around diaphragm 80. Such materials may be selected to provide a desired strength, flexibility, elasticity, and/or other mechanical properties. In addition, in some embodiments, a fabric liner may be placed over diaphragm 80. Such a liner may be selected to draw fluid out of upper section 40 and into distal section 60.

As shown, diaphragm 80 is shaped to comfortably conform to the shape of a patient's residual limb and the interior of intermediate section 60. For example, diaphragm 80 may include an upper surface 86 that is flat or concave, to conform to a distal portion of a residuum. In addition, diaphragm 80 may include a lower surface 88, having a convex shape configured to face away from a residual limb abutting upper surface 86. The lower convex surface 88 may be selected to form a fluid tight seal with at least part of intermediate section 60.

In some embodiments, it may be desirable to place a sealing sleeve 74 (as shown in FIG. 1) over the proximal opening of socket 30 and over a portion of the patient's residual limb. The sealing sleeve 74 may include any flexible fabric material and may fit snugly around the limb and socket to produce a fluid-tight seal. This may further increase the negative pressure created within socket 30. It should be noted however, that it may not be necessary to use a sealing sleeve to create suitable negative pressure if the patient's residual limb forms a sufficiently tight fit with socket 30. For example, some prosthetic sockets may include an annular ring made of a rubber or fabric material, including for example fluid-tight materials, and the annular ring may form a sufficient seal so that sleeve 74 is not needed. Such annular rings are included on, for example, Össur liners.

In many cases, a patient will place a fabric sleeve over the portion of the residual limb that is placed within socket 30.

Such sleeves may include a flexible fabric or other suitable material. The sleeve protects the patient's skin from irritation or excessive pressure. Further, the sleeve may increase the coefficient of friction between the limb and the socket wall, thereby ensuring a secure fit. A variety of suitable sleeve designs and materials are known in the art.

Figure 4A:
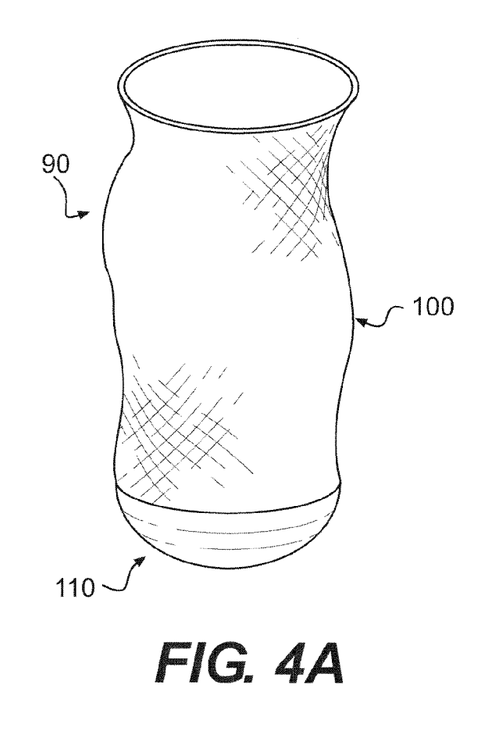
FIG. 4A illustrates a sleeve and diaphragm assembly that may be used with the prosthetic limbs of the present disclosure.

In some embodiments, it may be desirable to include a diaphragm with the sleeve, instead of providing socket 30 with a diaphragm 80. FIG. 4A illustrates a sleeve and diaphragm assembly 90 that may be used with the prosthetic limbs of the present disclosure. Assembly 90 may include an upper flexible tubular portion 100 that fits over a residual limb and a diaphragm 110 connected to upper portion 100.

Upper portion 100 may be produced from any suitable flexible material, as is known in the art. A number of different sleeve materials are available to protect residual limbs. Further, diaphragm 110 may include any suitable material, and diaphragm 110 may have a structure and material similar or identical to that of diaphragm 80, which is described with reference to FIG. 3A.

In some embodiments, diaphragm 110 may be permanently attached to upper portion 100. For example, diaphragm 110 may be attached to upper portion 100 using an adhesive, such as an acrylate-based adhesive, or any other suitable material.

Figure 4B:
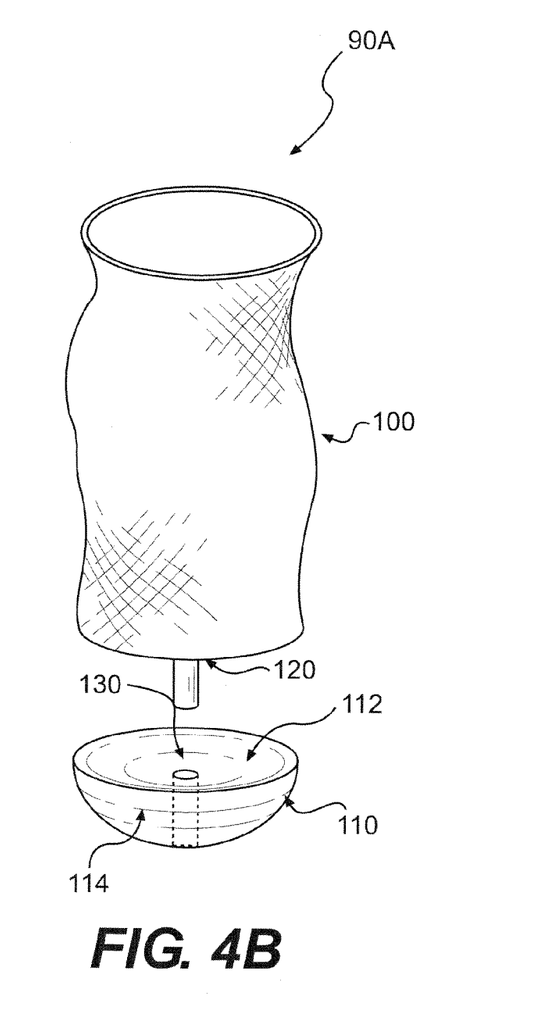
FIG. 4B illustrates a sleeve and diaphragm assembly that may be used with the prosthetic limbs of the present disclosure.

Alternatively, diaphragm 110 may be removably attached to upper portion 100. For example, FIG. 4B illustrates a sleeve and diaphragm assembly 90A that may be used with the prosthetic limbs of the present disclosure. As shown, upper portion 100 includes a connecting projection 120 that may be inserted into a receiving opening 130 of diaphragm 110. Connecting projection 120 and receiving opening 130 may include any suitable secure connecting mechanism, such as a threaded connection. Alternatively, other suitable connecting mechanisms may include, for example, loop and hook materials, vacuum systems, cohesion, threaded imbedded fixtures in diaphragm 80, and/or threaded-imbedded studs in diaphragm 80.

Figure 5:
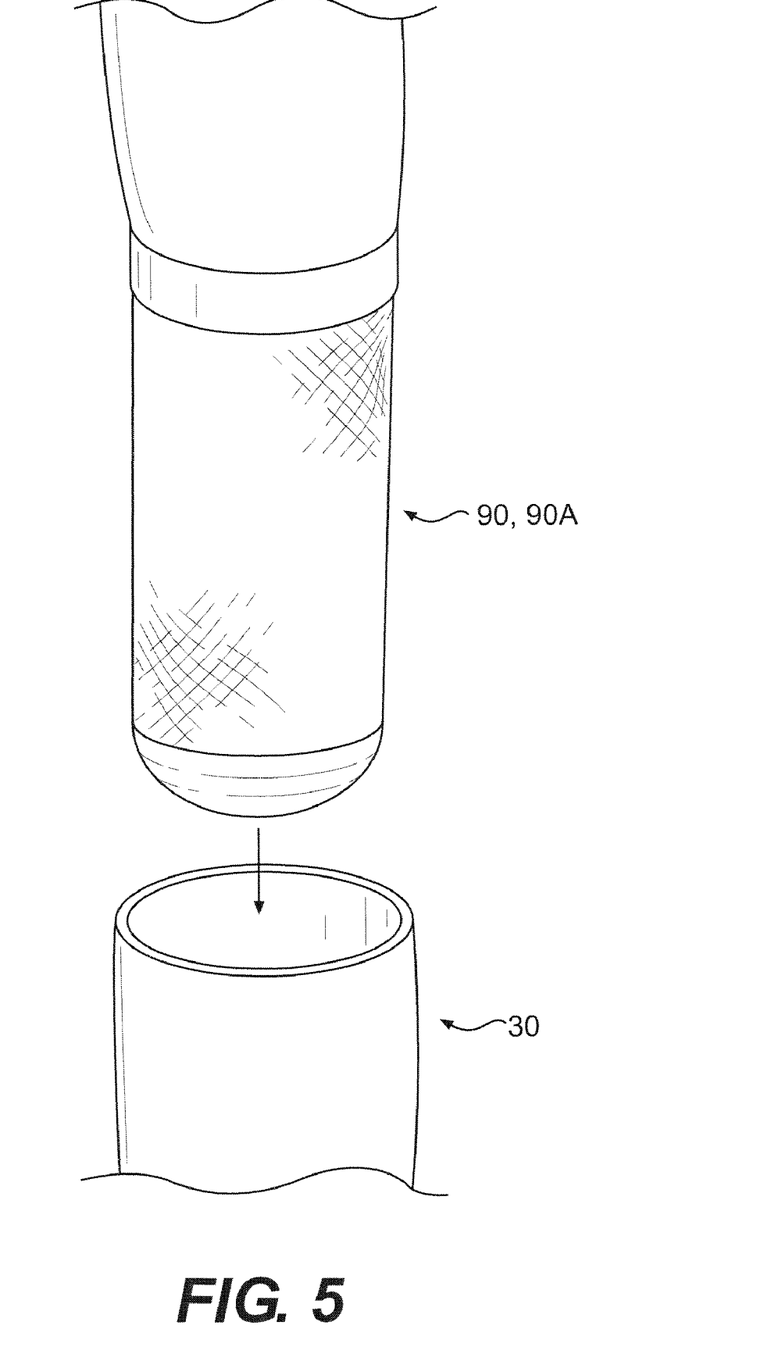
FIG. 5 illustrates the use of the sleeve and diaphragm assemblies of FIGS. 4A-4B with a prosthetic limb.

FIG. 5 illustrates the use of the sleeve and diaphragm assemblies 90 and 90A of FIGS. 4A-4B with a prosthetic limb. As shown, the assembly 90, 90A may be placed over a residual limb with the diaphragm permanently or detachably connected. A patient may then insert the limb, as covered with sleeve and diaphragm assembly 90, 90A into a prosthetic socket 30. In some embodiments, the socket will have a structure similar or the same as that described with reference to FIG. 2. Such sockets will include an elongated upper portion 40, and an intermediate portion 50 configured to receive diaphragm 110. The socket will further include a distal region 60 having a one-way valve 70. Further, as a patient's residual limb exerts downward pressure on diaphragm 110, diaphragm 110 may flex downward into third distal section 60. This downward pressure may force air out of valve 70, thereby producing a negative air pressure within socket 30.

In addition, like diaphragm 80, diaphragm 110 may be configured to comfortably conform to the shape of a residual limb and socket. For example, diaphragm 110 may include a concave upper surface 112 configured to contact a lower portion of upper tubular section 110 or a distal part of a residual limb. Further, diaphragm 110 may include a convex lower surface 114 configured to engage at least part of an interior surface of a socket assembly.

Figure 6:
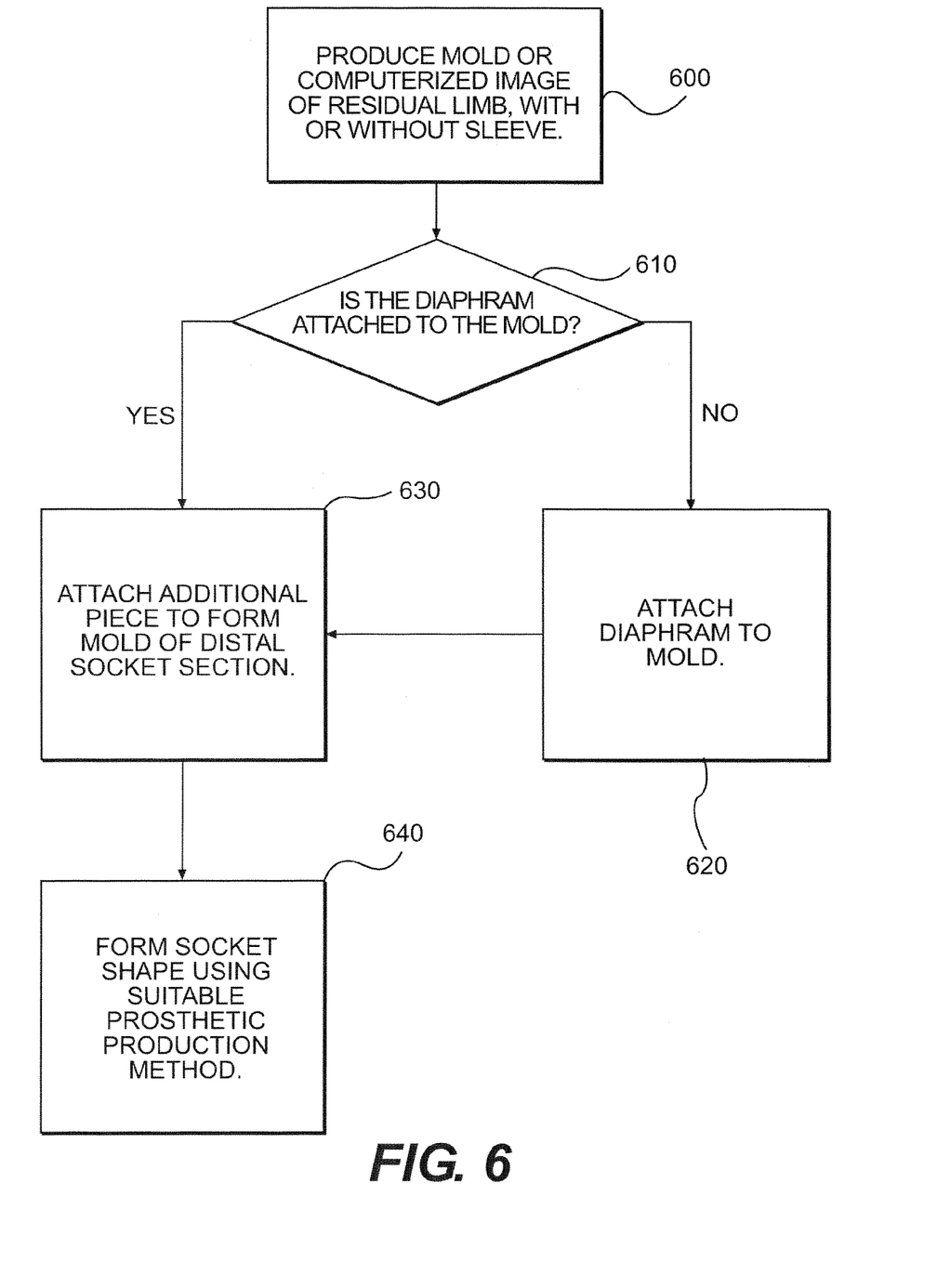
FIG. 6 illustrates a method of manufacturing a socket assembly for a prosthetic limb.

The socket assembly of the present disclosure may be produced using a number of techniques. For example, FIG. 6 illustrates a method of manufacturing a socket assembly, according to one embodiment. First, a prosthetist may produce a mold or image of a patient's residual limb, as shown at 600. Such molds or images may be produced using a variety of materials, such as a simple plaster or other materials known in the art. Further, more sophisticated methods, using computers and/or digital imaging systems may also be used. In one embodiment, the mold or image may be produced after a patient has placed a sleeve assembly 90,90A (as shown in FIGS. 4A-4B) over the residual limb. In this way, the mold will include the shape of diaphragm 80, 110.

Alternatively, the mold or image may be produced using a bare limb or limb having a sleeve without a diaphragm, as indicated at 610. If the prosthetist elects to produce the mold or image without the use of the diaphragm 80,110, a diaphragm, or material having a similar shape may be added to the mold or image so that a socket containing intermediate section 50, which conforms to the shape of diaphragm 80,100 may be produced, as indicated at 620. Next, a prosthetist may add an additional piece to the mold to represent distal section 60, as shown at 630.

Finally, having constructing a mold or image representing upper 40, intermediate 50, and distal sections 60 of socket 30, the prosthetist may form the outer wall of socket 30. A number of socket manufacturing techniques and materials are known in the art, and the prosthetist may select the material and production technique to form a socket having the shape of the as-constructed mold based on a number of factors. For example, such factors may include, cost, patient use, available materials and techniques, and/or desired socket strength or other mechanical properties.

It should be noted that as shown socket assembly 30 and prosthesis 10 are illustrated for a below the knee lower extremity prosthetic limb. However, the socket assembly, sleeve and prostheses of the present disclosure may be used for any suitable prosthetic limb, including below-the-knee prosthetic limbs, above-the-knee prosthetic limbs, or upper extremity prosthetics.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A socket assembly for connecting a residual limb to a prosthetic limb, comprising:
   an elongated upper circumferential section having an open upper end and a distal end;
   an intermediate section extending from the upper section and tapering inwardly to a lower rim region; and
   a distal section extending from the lower rim region to a base of the socket;
   a one-way valve in fluid communication with an interior of the socket assembly; and
   a flexible diaphragm engaging the lower rim region of the intermediate section forming a cavity in the distal section beneath the flexible diaphragm, wherein the diaphragm has a convex lower surface that maintains a convex shape without compression by a limb and is shaped to substantially conform to the inwardly tapering lower rim of the intermediate section, and wherein a portion of the convex surface is positioned over the distal section to allow deflection of a portion of the convex surface of the flexible diaphragm into and out of the cavity during routine movements.

2. The socket assembly of claim 1, wherein the diaphragm includes at least one opening providing fluid communication through the diaphragm.

3. The socket assembly of claim 1, wherein the diaphragm includes a polymeric material.

4. The socket assembly of claim 1, wherein the one-way valve is located on a lateral wall of the distal section.

5. The socket assembly of claim 1, wherein the one-way valve allows gas or fluid to flow only from inside the socket to outside the socket.

6. The socket assembly of claim 5, further including a mechanism to allow gas or fluid to flow from outside the socket to inside the socket.

7. The socket assembly of claim 1, wherein the one-way valve is positioned in a lateral wall of the upper section.

8. The socket assembly of claim 1, further including a flexible sleeve placed over the socket opening and over a portion of a patient's limb outside of the socket.

9. The socket assembly of claim 8, wherein the flexible sleeve is configured to provide a fluid seal to the socket.

10. The socket assembly of claim 1, further including an inner sleeve covering a portion of a patient's limb inside the socket and contacting the lateral wall of the upper section and an upper surface of the diaphragm.

11. The socket assembly of claim 1, wherein the diaphragm includes a concave upper surface.

12. A sleeve for a residual limb, comprising:
    an upper tubular flexible section formed of a first flexible material that can be placed over a residual limb; and
    a distal diaphragm securely connected to the upper flexible section and having a concave upper surface and a convex lower surface, wherein the distal diaphragm is formed of a second material having mechanical properties such that the diaphragm maintains a convex shape of the lower surface when compressive forces are not applied to the diaphragm by a residual limb, and when the diaphragm is positioned on a residual limb within a socket assembly to rest against an annular rim overlying a distal cavity in the socket assembly containing a one-way valve, a portion of the convex lower surface of the distal diaphragm is deflected into and rebounds out of the cavity during routine movements and produces a negative pressure within the socket assembly.

13. The sleeve of claim 12, wherein the diaphragm is permanently connected to the upper section.

14. The sleeve of claim 12, wherein the diaphragm is removably connected to the upper section.

15. The sleeve of claim 12, wherein the diaphragm includes at least one opening providing fluid communication through the diaphragm.

16. The sleeve of claim 12, wherein the diaphragm includes a polymeric material.

17. A prosthetic limb, comprising:
    a socket assembly, including:
        an elongated upper circumferential section having an open upper end and a distal end;
        an intermediate section extending from the upper section and tapering inwardly to a lower rim region; and
        a distal section extending from the lower rim region to a base of the socket; and
        a one-way valve in fluid communication with an interior of the socket assembly;
    a flexible diaphragm engaging the lower rim region of the intermediate section forming a cavity in the distal section beneath the flexible diaphragm, wherein the diaphragm has a convex lower surface that maintains a convex shape without compression by a limb and is shaped to substantially conform to the inwardly tapering lower rim of the intermediate section, and wherein a portion of the convex surface is positioned over the distal section to allow deflection of a portion of the convex surface of the flexible diaphragm into and out of the cavity during routine movements; and
    an elongated shaft securely attached to the socket assembly.

18. The prosthetic limb of claim 17, further including a flexible diaphragm configured to engage walls of the intermediate section.

19. The prosthetic limb of claim 17, wherein the diaphragm includes at least one opening providing fluid communication through the diaphragm.

20. The prosthetic limb of claim 17, wherein the diaphragm includes a polymeric material.

21. The prosthetic limb of claim 17, wherein the one-way valve is located on a lateral wall of the distal section.

22. The prosthetic limb of claim 17, wherein the one-way valve allows gas or fluid to flow only from inside the socket to outside the socket.

23. The prosthetic limb of claim 22, further including a mechanism to allow gas or fluid to flow from outside the socket to inside the socket.

24. The prosthetic limb of claim 17, wherein the one-way valve is positioned in a lateral wall of the distal section.

25. The prosthetic limb of claim 17, further including a flexible sleeve placed over the socket opening and over a portion of a patient's limb outside of the socket.

26. The prosthetic limb of claim 25, wherein the flexible sleeve is configured to provide a fluid seal to the socket.

27. The prosthetic limb of claim 17, further including an inner sleeve covering a portion of a patient's limb inside the socket and contacting the lateral wall of the upper section and an upper surface of the diaphragm.

28. The socket of claim 1, wherein deflection of the diaphragm into and out of the cavity during routine movements produces a negative pressure within the socket is sufficient to control for limb volume changes during use.

29. The socket of claim 1, wherein the diaphragm has a thickness that increases from a peripheral edge to the center of the diaphragm.

30. The sleeve of claim 12, wherein deflection of the diaphragm into and out of the cavity during routine movements produces a negative pressure within the socket that is sufficient to control for limb volume changes during use.

31. The sleeve of claim 12, wherein the diaphragm has a thickness that increases from a peripheral edge to the center of the diaphragm.

32. The prosthetic limb of claim 17, wherein deflection of the diaphragm into and out of the cavity during routine movements produces a negative pressure within the socket that is sufficient to control for limb volume changes during use.

33. The prosthetic limb of claim 17, wherein the diaphragm has a thickness that increases from a peripheral edge to the center of the diaphragm.

34. A socket assembly for connecting a residual limb to a prosthetic limb, comprising:
    an elongated upper circumferential section having an open upper end and a distal end;
    an intermediate section extending from the upper section and tapering inwardly to a lower rim region; and
    a distal section extending from the lower rim region to a base of the socket;
    a one-way valve in fluid communication with an interior of the socket assembly; and
    a flexible diaphragm engaging the lower rim region of the intermediate section forming a cavity in the distal section beneath the flexible diaphragm, wherein the diaphragm has a shape and mechanical properties selected to allow deflection of a portion of the flexible diaphragm into and out of the cavity during routine movements that produces a negative pressure within the socket that is sufficient to control for limb volume changes during use.

35. The socket assembly of claim 34, wherein the diaphragm includes at least one opening providing fluid communication through the diaphragm.

36. The socket assembly of claim 34, wherein the diaphragm includes a polymeric material.

37. The socket assembly of claim 34, further including a flexible sleeve placed over the socket opening and over a portion of a patient's limb outside of the socket.

38. The socket assembly of claim 34, further including an inner sleeve covering a portion of a patient's limb inside the socket and contacting the lateral wall of the upper section and an upper surface of the diaphragm.

39. The socket assembly of claim 34, wherein the diaphragm includes a concave upper surface and a convex lower surface.

* * * * *